United States Patent [19]

Takiguchi

[11] Patent Number: 4,797,192

[45] Date of Patent: Jan. 10, 1989

[54] ION SELECTIVE ELECTRODE APPARATUS WITH AN EARTH ELECTRODE

[75] Inventor: Toshio Takiguchi, Tochigi, Japan

[73] Assignee: Kabushiki Kaisha Toshiba, Kawasaki, Japan

[21] Appl. No.: 74,188

[22] Filed: Jul. 16, 1987

[30] Foreign Application Priority Data

Jul. 18, 1986 [JP] Japan ................................ 61-169324
Jul. 22, 1986 [JP] Japan ................................ 61-170822

[51] Int. Cl.$^4$ ............................................ G01N 27/26
[52] U.S. Cl. ................................. 204/412; 204/416;
                                    204/418; 204/419; 204/435
[58] Field of Search ............... 204/412, 416, 418, 419,
                                                    204/435, 409

[56] References Cited

U.S. PATENT DOCUMENTS 3,862,895  1/1975  King et al. ........................ 204/412
4,409,088 10/1983  Kanno et al. ..................... 204/402
4,533,457  8/1985  Watanabe .......................... 204/416

Primary Examiner—John F. Niebling
Assistant Examiner—Kathryn Gorgos
Attorney, Agent, or Firm—Cushman, Darby & Cushman

[57] ABSTRACT

An ion selective electrode apparatus for measuring ion activity of solution flowing through a conduit, wherein at least one earth electrode is disposed so as to contact the solution. The earth electrode is capable of shunting electrical noise flowing through the conduit to earth. In the preferred embodiment, an ion selective electrode and a reference electrode are disposed along the conduit between two earth electrodes so as to protect the ion selective and reference electrodes from the electrical noise which may be introduced into the ends of the conduit.

8 Claims, 4 Drawing Sheets

ION SELECTIVE ELECTRODE APPARATUS WITH AN EARTH ELECTRODE

BACKGROUND OF THE INVENTION

1. Field of the Invention

This invention relates to an ion selective electrode apparatus having an earth electrode for reducing noise leaked to the ion selective electrode, and, more particularly, to an earth electrode for an ion selective apparatus of the flowthrough type.

2. Discussion of the Prior Art

Ion selective electrodes combined to constitute an ion selective electrode apparatus are generally used to electrochemically detect the activity of ions like sodium, potassium cation or chloride anion in blood. The concentrations of these ions in blood of healthy or normal human beings lie in respective narrow ranges. In other words, an abnormal concentration of these ions indicates disease or malfunction of body organs. Actually, they provide diagnostic proof or information for determining, for example, the presence of kidney troubles, myocardial infarction, or manic depressive psychosis. The measurement of activity of ions in the blood indicates the concentration of the ions, for the concentration of ions is proportional to their activity.

An ion selective electrode apparatus usually comprises an ion selective electrode and a reference electrode. The ion selective electrode includes an ion selective membrane on the surface of it. The ion selective membrane has holes as large as a specific ion and has an opposite polarity to that of the ion. The holes in the membrane tend to capture the specific ions for a longer time than any other ions. The reference electrode, on the other hand, keeps a constant voltage difference across the solution so that the specific ions dissolve. When both the ion selective and reference electrodes are immersed in the solution, the potential of the ion selective electrode is different from that of the reference electrode. As a result, the electrodes induce a potential E related to the activity A of a specific ionic species present in the solution, as shown by the Nernst equation:

$$E = E_0 \pm 2.303 \, (RT/ZF) \log A$$

Wherein R, T, Z, F, and $E_0$ represent the gas constant, the temperature of the solution expressed in terms of the absolute temperature, the ionic valence of the specific ion species, the Faradic constant, and the potential of the reference electrode, respectively. The (+) sign is employed when A is induced by cationic activity, and the (−) sign is employed when A is induced by anionic activity. As a result, the activity of the specific ion species can be readily calculated according to the Nernst equation.

An ion selective electrode apparatus of the flowthrough type is available in the prior art for an automatic chemical analyzer which automatically analyzes many samples such as patient serums according to a number of items. Such an ion selective electrode is taught in U.S. Pat. No. 4,533,457 issued to Watanabe. The electrode apparatus taught by Watanabe includes a tube of substantial size where the samples flow. The inner peripheral surface includes a plurality of ion selective electrodes and a reference electrode, and when the samples flowthrough the tube, the activities of the several kinds of ions are simultaneously obtained from the potentials between the respective electrodes and the reference electrode. This type of selective electrode apparatus is compact and is useful for measuring many samples for a number of analysis items in a short period of time. However, in this conventional electrode apparatus, electrical noise may leak to the electrode via the flowthrough.

Since an ion selective electrode has a high input impedance, an electrical noise impinged on it adversely affects the measurement of the activity of an ion. Therefore, the electrical noise introduced via the flowthrough makes the measurement of activity of a certain ion less accurate.

SUMMARY OF THE INVENTION

It is an object of the present invention to provide an ion selective electrode apparatus with an earth electrode through which electrical noise may be grounded.

It is another object of the present invention to provide an ion selective electrode apparatus of the flowthrough type with two earth electrodes disposed at the entrance and exit of it so that such electrical noise may be grounded.

To accomplish the above objects, an ion selective electrode apparatus according to the present invention comprises a block having a conduit through which a sample solution flows. A reference electrode for keeping a constant voltage applied to the solution sample is disposed in the conduit so that the reference electrode is in contact with the sample solution. An ion selective electrode for inducing a potential related to the activity of a specific ion with respect to the reference electrode is juxtaposed in the conduit so that the ion selective electrode contacts the sample solution. An earth electrode is then disposed at one of or both entrance and exit of the conduit for grounding the electrical potential to ground.

DESCRIPTION OF THE PREFERRED EMBODIMENTS

Figure 1:
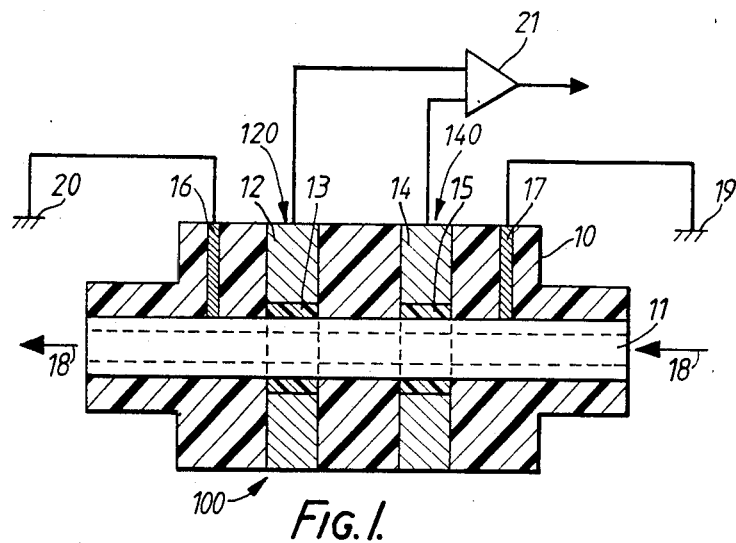
FIG. 1 is a sectional view illustrating the construction of a first embodiment of an ion selective electrode apparatus with earth electrodes according to the present invention.

Now referring to FIG. 1, the first embodiment of an ion selective electrode apparatus 100 according to the preeent invention will be explained. A block 10 made of electrically insulating material has a conduit 11 through which a sample solution such as patient serum is diluted by a buffer. The sample solution flows through the conduit 11 in the direction 18. Also, in block 10, an ion selective electrode 120 and a reference electrode 140 are disposed so as to enclose the conduit 11. The ion selective electrode 120 includes an ion selective membrane 13 chosen by an ion to be measured.

In the case of measurement of the concentration of a chlorine-ion electrode, a solution of 1.8 to 2.3 weight % of methyl tridodecyl ammonium chloride, 6.7 to 7.2 weight % of polyvinyl chloride, and 91 weight % of tetrahydrofuran is applied to a surface of a metal layer 12. Tetrahydrofuran is removed by vaporization. Thus, the membrane 13 of a thickness of 20 $\mu$m to 50 $\mu$m and sensitive to a chlorine ion is formed.

In the case of measurement of the concentration of a potassuim-ion electrode, a solution of 0.2 to 0.5 weight % of valinomycin, 4.5 to 5.4 weight % of a plasticizer such as dioctyl adipate, 3.7 to 4.5 weight % of polyvinyl chloride, and 89.7 to 91.7 weight % of tetrahydrofuran is applied to the surface of the metal layer 12. Tetrahydrofuran is removed to form a membrane 13 of a thickness of 20 $\mu$m to 50 $\mu$m and sensitive to a potassium ion.

In the case of measurement of the concentration of a sodium-ion electrode, on the other hand, a solution of 0.2 to 0.5 weight % of monensin, 4.5 to 5.4 weight % of a plasticizer such as dioctyl adipate, 3.7 to 4.5 weight % of polyvinyl chloride, and 89.7 to 91.7 weight % of tetrahydrofuran is applied to the surface of the metal layer 12. Tetrahydrofuran is again removed to form membrane 13 of a thickness of 20 $\mu$m to 50 $\mu$m and sensitive to a sodium ion.

The ion selective electrode 120 thus formed is disposed in the block 10 so that the membrane 13 contacts the sample solution flowing through the conduit 11. The metal layer 12 is connected to an amplifier 21 having a high input impedance, such as a differential amplifier.

A reference electrode 140 also is disposed in the block 10 to enclose the inside of the conduit 11. The reference electrode 140 comprises a membrane 15 and a metal layer 14. A mixture of a suspension of 29 weight % of potassium chloride, 7 weight % of polyvinyl chloride and 64 weight % of tetrahydrofuran is applied to a surface of a metal layer 14 having silver and silver chloride thereon. After the tetrahydrofuran is removed by vaporization, a thin layer containing potassium chloride is left on the silver chloride film. Next a solution of polyvinyl chloride and tetrahydrofuran is applied to the surface of the thin layer containing potassium chloride, and the tetrahydrofuran is again removed by vaporization. Then a polyvinyl chloride film is formed on the thin layer containing potassium chloride film as a protective film. This thin layer forms the membrane 15 on the surface of the metal layer 14.

The reference electrode 140 is disposed in the block 10 so that the membrane 15 contacts the sample solution flowing through the conduit 11. The metal layer 14 of the reference electrode is connected to another input of the amplifier 21.

Two earth electrodes 16 and 17 are disposed at the entrance and exit of the block 10 so that they contact the sample of solution flowing through the conduit 11. The earth electrodes 16 and 17 are made of a stain-proof material such as platinum or carbon and are respectively grounded to earths 19 and 20 as shown.

The sample solution flows through the conduit 11 in the direction 18. A potential related to the activity of the ion corresponding to the ion selective electrode 120 rises between the ion selective electrode 120 and the reference electrode 140. The amplifier 21 then amplifies the potential and provides it to a data processing unit (not shown) for displaying the activity of the ion digitally on a monitor or for printing it out.

When different sample solutions are successively analyzed, a calibrating solution of a known ion activity flows through the conduit 11 after each sample solution flows through it. The calibrating solution is used not only for the calibration of the ion seleceive electrode apparatus 100, but also for the cleaning of the inside of the conduit 11 to prevent contamination with a previous sample solution.

A solution may contain electrical noise which comes through the entrance 16 or the exit 7. This electrical noise is grounded to the earths 9 and 20 because the input impedance of the earth electrodes 19 and 20 are much smaller than that of the ion selective electrode 120 and the reference electrode 140. Therefore, the electrical noise coming from the entrance or exit of the conduit 11 is not received by the electrodes 120 and 140 due to the effects of grounding the noise.

Figure 2:
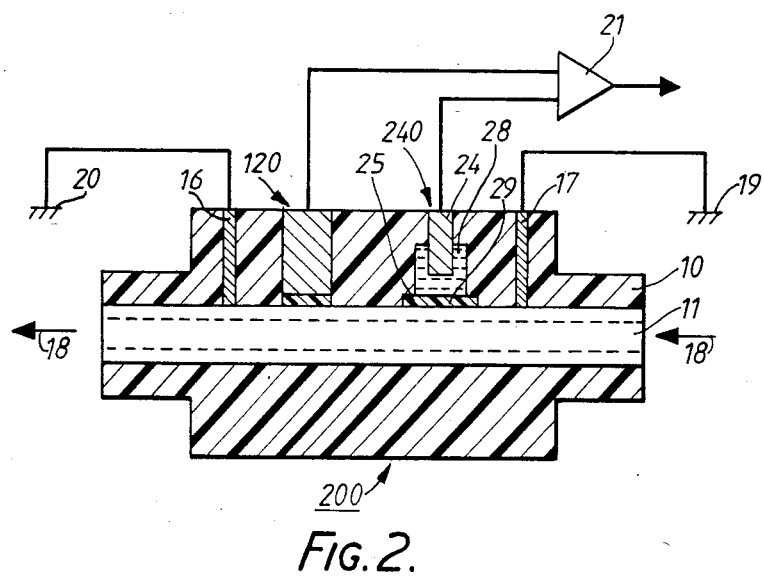
FIG. 2 is a sectional view illustrating the construction of a second embodiment of an ion selective electrode apparatus with earth electrodes according to the present invention.

Referring to FIG. 2, the second embodiment 200 of the ion selective electrode according to the present invention will be explained. In this second embodiment 200, the reference electrode 240 is different from that of the first embodiment 100. The reference electrode 240 includes a vessel 29 in the conduit 10 for holding a reference liquid 28 such as saturated potassium chloride. This vessel 29 is covered by a lid 25 made of a porous material such as ceramic. This porous lid 25 allows the reference liquid 28 to contact the sample solution without losing the reference liquid 28. This contact thus forms a liquid junction for generating a liquid junction potential between the sample solution and the reference liquid 28. The reference potassium chloride liquid causes the junction to generate only a small potential which does not depend on the activities of any of the ions. In other words, it generates a reference potential. This reference potential is picked up by metal electrode 24, which is made of silver and silver chloride or the like, and the metal electrode 24 is inserted into the reference liquid 28 of the vessel 29. The metal electrode 24 is also electrically connected to the amplifier 21.

This reference electrode 240 is stable with respect to the sample solution because of the liquid junction. Waste material in the sample solution is thus less likely to adhere to the surface of the reference electrode 240 than the solid type electrode 140 in the first embodiment. Accordingly, this reference electrode 240 may be used for a long time without maintenance.

Figure 3:
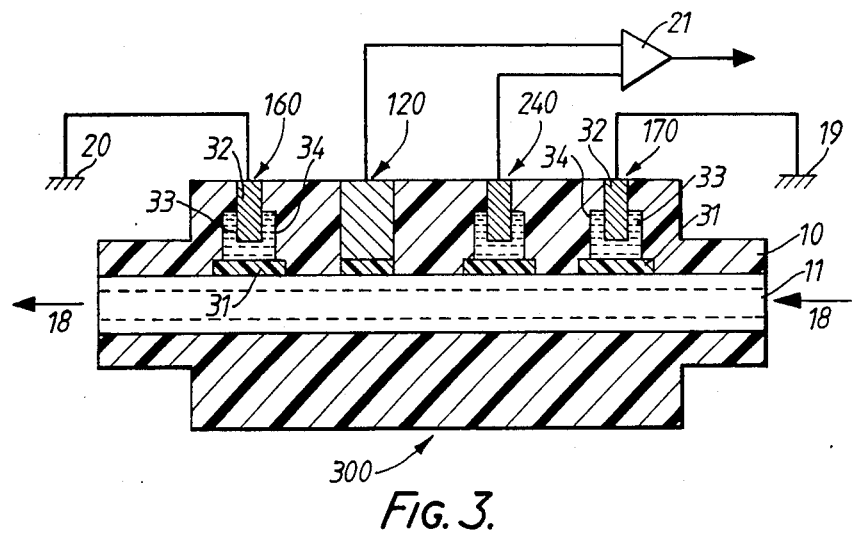
FIG. 3 is a sectional view illustrating the construction of a third embodiment of an ion selective electrode apparatus with earth electrodes according to the present invention.

Referring now to FIG. 3, the third embodiment 300 of the ion selective electrode according to the present invention is shown. In this embodiment 300, earth electrodes 160 and 170 as well as the reference electrode 240 the second embodiment are liquid type electrodes. Each of the earth electrodes 160 and 170 includes a vessel 34 engraved in the conduit 10. The vessel 34 holds a liquid 33 similar to the reference liquid. A porous lid 31 covers the vessel 34, but it keeps a liquid contact between the sample solution and the liquid 33. A metal electrode 32 made of silver and silver chloride or the like is inserted into the liquid 33 and is electrically connected to earths 19 and 20. Since the input impedance of the earth electrodes 160 and 170 grounded to earths 19 and 20 is much lower than that of the ion selective electrode 120 or the reference electrode 240 connected to the amplifier 21, electrical noise coming through the conduit 11 is captured by these earth electrodes 160 and 170 and is not received by either the ion selective electrode 120 or the reference electrode 240. In this manner, earth electrodes 160 and 170 can function a long time for the same reason as the reference electrode 240 described above.

Figure 4:
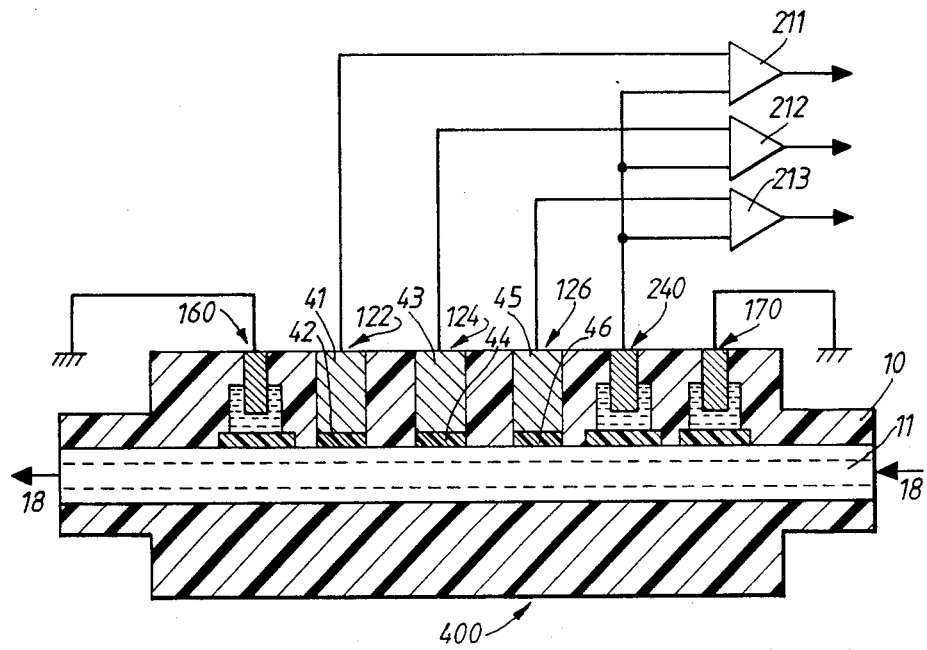
FIG. 4 is a sectional view illustrating the construction of a fourth embodiment of an ion selective electrode apparatus with earth electrodes according to the present invention.

FIG. 4 shows a fourth embodiment 400 of the ion selective electrode according to the present invention. This embodiment 400 includes three different ion selective electrodes 122, 124 and 126 for three different ions such as sodium, potassium and chloride. Each electrode has a surface with metal layers 41, 43 and 45, respectively, each being made of, for example, platinum, gold, copper, etc. The respective metal layers are coated with the respective membranes 42, 44 and 46. The membranes 42, 44 and 46 are respectively sensitive to sodium, potassium and chloride ions and are made by the processes described above with reference to the first embodiment 100. Also, each of the metal layers 41, 43 and 45 is connected to one input of respective amplifiers 211, 212 and 213. The other input of each amplifier 211, 212 and 213 is commonly connected to the reference electrode 240. Thus, these amplifiers 211, 212 and 213 amplify the respective potentials detected by the ion selective electrodes 122, 123 and 124 to provide input to a data processing unit (not shown). This embodiment 400 is thus capable of measuring three different ions simultaneously.

Figure 5:
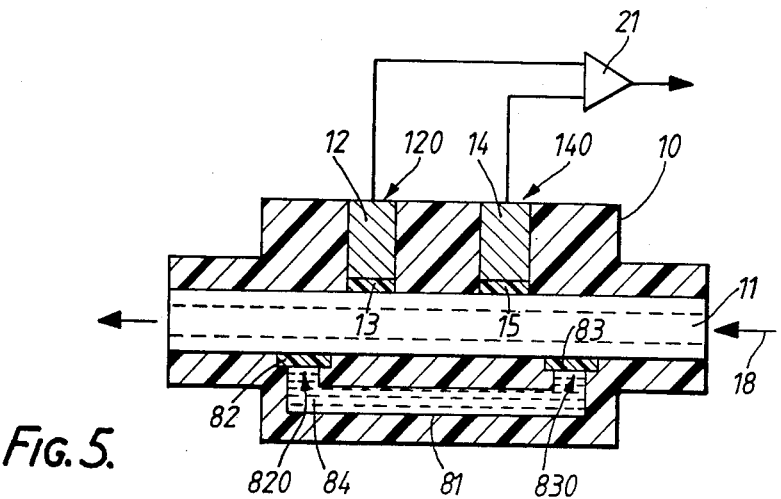
FIG. 5 is a sectional view illustrating the construction of a fifth embodiment of an ion selective electrode apparatus with earth electrodes according to the present invention.

The earth electrode of the embodiments described above is grounded to earth, but this is not essential to the present invention. In the fifth embodiment as shown in FIG. 5, for example, earth electrodes 820 and 830 are connected to each other by a U shaped pipe 81 disposed in the block 10. The earth electrodes 820 and 830 comprise the respective porous lids 82 and 83 made of a material like the material of the lid 25 which covers both ends of the pipe 81. Thus, the pipe 81 is filled with a reference liquid, and the lids 82 and 83 form the respective liquid junctions between the liquid in the pipe 81 and the solution in the conduit 11.

Since the input impedance between the earth electrodes 820 and 830 is much lower than that of the ion selective electrode 120 or the reference electrode 140 disposed between them, electrical noise flows through the pipe 81 and does not impinge on the electrodes 120 and 140. In other words, the electrical noise bypasses the electrodes 120 and 140 by flowing through the pipe 81.

When the earth electrodes are made of metal such as that used for electrodes 16 and 17, the pipe 81 may be replaced by an electrically conductive wire. In such an arrangement, the electrical noise flows through the wire without impinging on the ion selective or reference electrode.

The embodiments described above include two earth electrodes disposed at the entrance and exit, respectively, of the conduit 11. However, if one of the flowing lines is a short distance from ground or is open (i.e., it is expected that little electrical noise comes from the flow), one of the earth electrodes is dispensable.

Now, referring to FIGS. 6 and 7, the sixth embodiment of the ion selective electrode according to the present invention will be explained.

A chain of cups 60 circulates in the direction 62 through a series comprised of a sample suction section, a reagent dilution section, a reaction section, an analysis section and a cleaning section. At the sample suction section, several different samples are pipetted into cups for each of the items to be analyzed. Then at the reagent dilution section, the samples are diluted by the respective reagents according to the item under analysis. Every cup following a cup holding the sample solution for ion analysis is loaded with a calibrating liquid. The reaction section also keeps the cups loaded with the sample solution over the range between 25° C. and 37° C. to promote the chemical reaction of the sample and the respective reagent. Next, the sample solutions are biochemically analyzed by, for example, a spectrometer and a photometer as well as the ion selectrode apparatus. Finally, the cups are cleaned by deionized water and dried at the cleaning section.

Figure 7:
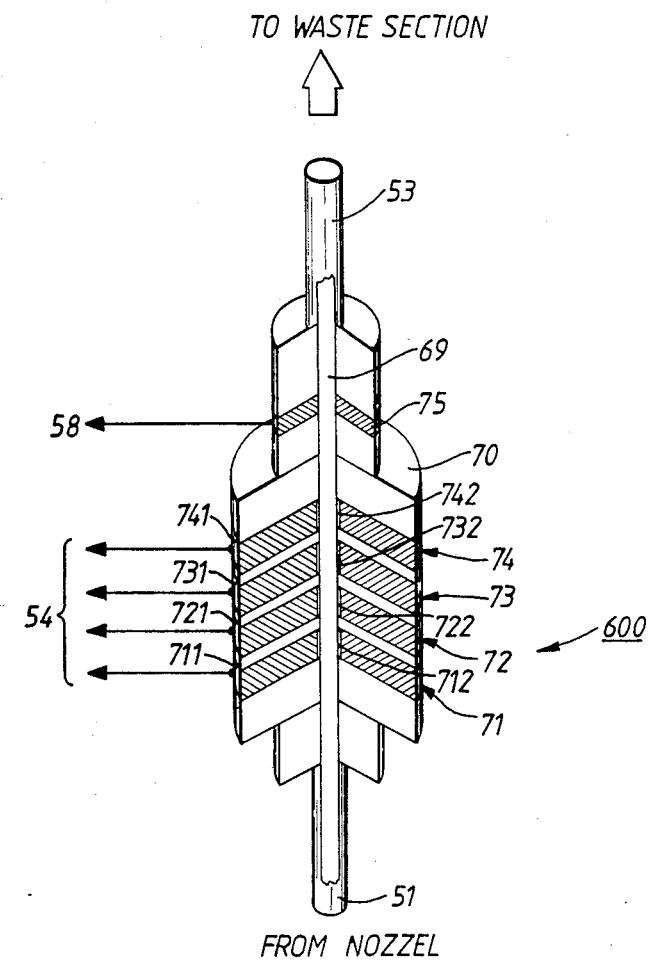
FIG. 7 is a partially cut-away perspective view illustrating the construction of a sixth embodiment of the ion selective electrode apparatus with a single earth electrode for use in an automatic chemical analyzer such as that shown in FIG. 6.

In the analysis section, a box 52 containing an ion selective electrode apparatus as shown in FIG. 7 ascends and descends in the direction 61 by a drive mechanism (not shown). The box 52 has a nozzle 51 in the bottom of it. The nozzle 51 is connected to a syringe pump (not shown) through a tube 53 so as to suck the sample solution for the ion analysis and the calibrating liquid for the calibration of the ion selective electrode apparatus from the cup. The sucked sample solution and the calibrating liquid flowthrough the ion selective electrode apparatus 600 in the box 52 and are discharged through the tube 53 into a waste section (not shown).

Figure 6:
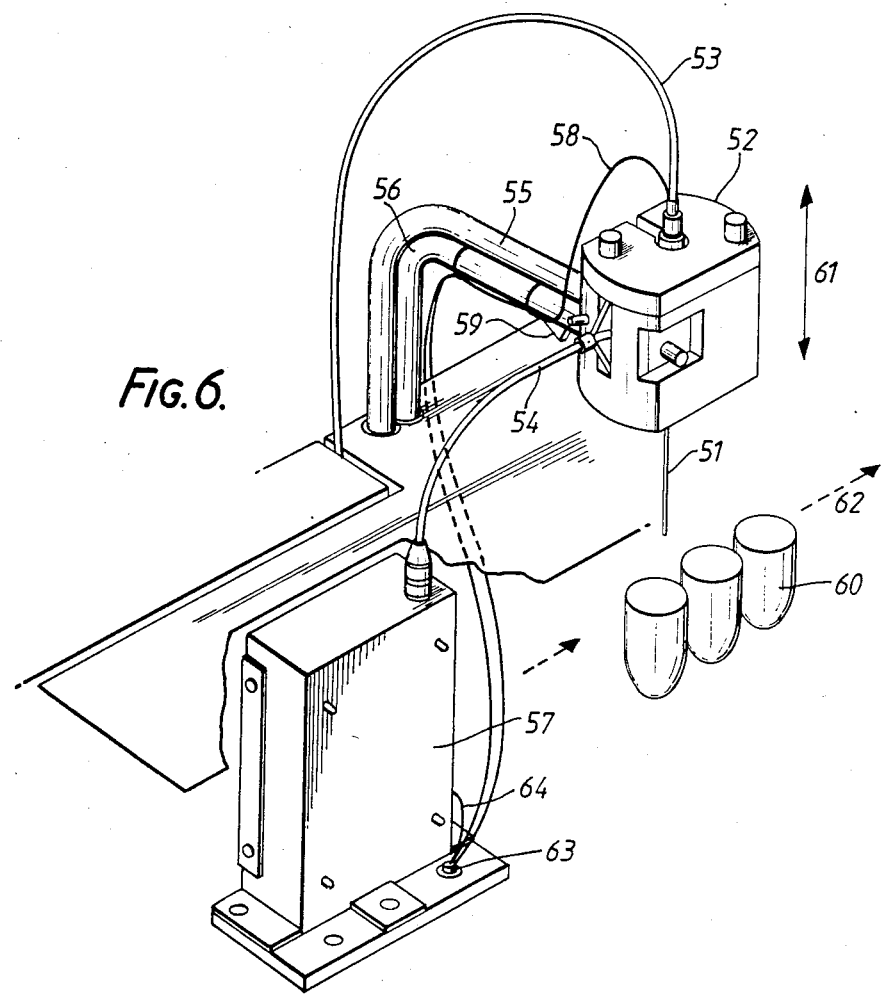
FIG. 6 is a perspective view of the ion analyzing section of an automatic chemical analyzer.

The ion selective electrode apparatus 600 in the box 52 as shown in FIG. 6 includes block 70 having a conduit 69, one end of which is connected to the nozzle 51 and the other of which is connected to the tube 53. In the block 70, one reference electrode 71, three different ion-selective electrodes 72, 73 and 74 and earth electrode 75 are juxtaposed along the conduit 69 so that their inside surfaces contact the sample solution flowing through the conduit 69. The reference electrode 71 includes a metal layer 711 and the membrane 712 on the inside surface of the metal layer 711 and generates a reference potential which is provided to an amplifier box 57 through cables 54. The three different ion-selective electrodes 72, 73 and 74 include the metal layers 721, 731 and 741 and the membranes 722, 732 and 742, respectively. The membranes 722, 732 and 742 are made by the process described with reference to the first embodiment 100 and are sensitive to the respective sodium, potassium and chloride ions. The metal layers 721, 731 and 741 are connected to the respective amplifiers (not shown) in the amplifier box 57 through the cables 54. At the exit of the conduit 69, the earth electrode 75 made of a chemically stable and electrically conductive material such as platinum, carbon and the like is connected to earth 63 through earth cable 58 extending from the box 57 to earth 63.

The box 52 including the ion selective electrode apparatus 600 is grounded to earth 63 through earth cable 59. A warm liquid also circulates around the box 52 through tubes 55 and 56 to keep the temperature of the ion selective electrode apparatus 600 in the range of 25° C. to 37° C. The amplifier box 57 is also grounded to earth 63 through earth cable 64.

When the cup 60 loaded with the sample solution for the measurement of ion activities of the specific ions comes to the position underneath the nozzle 51, the box 52 descends from the home position towards the cup 60 to suck the sample solution from the cup 60. While the sample solution flows through the conduit 69 of the ion selective electrode apparatus 600, the ion selective electrodes 72, 73 and 74 generate the potentials related to the ion activities with respect to the reference potential provided from the reference electrode 71. The potentials are provided to the amplifiers in the amplifier box 57. After that, the box 52 ascends to the home position, and the next cup 60 loaded with the calibrating liquid comes underneath the nozzle 51. The nozzle 51 again descends to suck the calibating liquid. The electrodes 71 to 74 are calibrated and cleaned by the calibrating liquid. This process is repeated until the last sample solution is tested and the data relating to the ion activities are processed by the data processing unit (not shown). The results of the measurement of the ion activities are then displayed on a monitor or printed out item by item.

In this embodiment (FIGS. 6 and 7), the earth electrode 75 is disposed only at the exit of the conduit 69, since the nozzle disposed at the entrance of the conduit 69 is short and electrically open, thereby causing little electrical noise to come from the nozzle 51. Accordingly, the single earth electrode 75 is capable of shunting the electrical noise coming from the flowing input. Thus, it is not necessary to dispose another earth electrode at the entrance of the conduit 69 in this case; however, it may be desirable to do so if too much noise is being generated for grounding by a single earth electrode.

Although only a few exemplary embodiments of this invention have been described in detail above, those skilled in the art will readily appreciate that many modifications are possible in the preferred embodiments without materially departing from the novel teachings and advantages of this invention. Accordingly, all such modifications are intended to be included in this invention as defined by the following claims.

What we claim is:

1. An apparatus for measuring ion activity in a solution to be examined, comprising:
   a block having a conduit through which the solution flows;
   reference electrode means, disposed in said block so as to contact the solution flowing through the conduit, for generating a first potential as a reference potential of the solution independent of the activity of the solution;
   ion selective electrode means, disposed adjacent to said reference electrode means in said block so as to contact the solution flowing through the conduit for generating a second potential dependent on the activity of the solution;
   first earth electrode means disposed in said block in electrical contact with the solution flowing through the conduit and downstream of both said reference electrode means and said ion selective electrode means; and
   second earth electrode means disposed in said block in electrical contact with the solution flowing through the conduit and upstream of both said reference electrode means and said ion selective electrode means.

2. The apparatus according to claim 1, wherein each of said earth electrode means includes:
   a vessel for holding a liquid;
   a porous lid covering the vessel for establishing a liquid junction between the solution flowing through the conduit and the liquid of said vessel; and
   a metal electrode inserted into the liquid of the vessel for picking up the potential of the liquid junction.

3. The apparatus according to claim 1, wherein at least one of said first and second earth electrode means surrounds an inside surface of the conduit.

4. The apparatus according to claim 2, wherein said first and second earth electrode means are connected to each other by a pipe filled with a liquid.

5. The apparatus according to claim 1, wherein both said first and second earth electrode means are grounded to common earth.

6. The apparatus according to claim 1, wherein said first and second earth electrode means have a lower impedance than said reference and ion selective electrode means.

7. An apparatus for measuring ion activity in a solution to be examined, comprising:
   a block having a conduit through which the solution flows, one and of said conduit being electrically open;
   reference electrode means, disposed in said block so as to contact the solution flowing through the conduit, for generating a first potential as a reference potential of the solution independent of the activity of the solution;
   ion selective electrode means disposed adjacent to said reference electrode means in said block so as to contact the solution flowing through the conduit for generating a second potential dependent on the activity of the solution;
   earth electrode means, disposed in said block in electrical contact with the solution flowing through the conduit and at a side of both said reference electrode means and said ion selective electrode means opposite said electrically open end of said conduit relative to a direction of solution flow, for electrically grounding the solution contacting thereto.

8. The apparatus according to claim 7, further comprising a nozzle connected to said one side of the conduit which is electrically open and means for causing said nozzle to move down and up toward a cup loaded with the solution to enable the nozzle to suck the solution.

* * * * *